United States Patent [19]

Crawley

[11] Patent Number: 4,548,888
[45] Date of Patent: Oct. 22, 1985

[54] PHOTOGRAPHIC PRODUCTS EMPLOYING NOVEL NONDIFFUSIBLE HYDRAZONE DYE-RELEASING COMPOUNDS

[75] Inventor: Michael W. Crawley, Watford, England

[73] Assignee: Eastman Kodak Company, Rochester, N.Y.

[21] Appl. No.: 669,144

[22] Filed: Nov. 7, 1984

[30] Foreign Application Priority Data

Dec. 20, 1983 [GB] United Kingdom ................ 8333830

[51] Int. Cl.$^4$ .......................... G03C 1/40; G03C 5/54
[52] U.S. Cl. .................................... 430/223; 430/222; 430/224; 430/225; 430/226; 430/559; 430/562
[58] Field of Search ............... 430/222, 223, 224, 225, 430/226, 559, 562

[56] References Cited

U.S. PATENT DOCUMENTS

| | | | |
|---|---|---|---|
| 3,628,952 | 12/1971 | Puschel et al. | 430/223 |
| 3,736,136 | 5/1973 | Danhauser et al. | 430/240 |
| 3,953,211 | 4/1976 | Imai et al. | 430/225 |

OTHER PUBLICATIONS

"Preconcentration of Trace Metal Ions by Combined Complexation-Anion Exchange Part I, Cobalt, Zinc and Cadmium with 2-(3'-Sulfobenzoyl-)-Pyridine-2-Pyridylhydrazone", *Anal. Chem. Acta*, 81, (1976), pp. 349-360 by Going, Wesenberg and Andrejat.

*Primary Examiner*—Richard L. Schilling
*Attorney, Agent, or Firm*—Harold E. Cole

[57] ABSTRACT

Photographic elements, diffusion transfer assemblages, coordination complexes and processes are described which employ a novel nondiffusible hydrazone compound capable of releasing at least one diffusible yellow dye or dye precursor thereof having the formula:

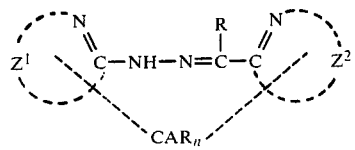

wherein:
(a) $Z^1$ and $Z^2$ each independently represents the atoms necessary to complete a 5- or 6-membered aromatic heterocyclic ring;
(b) CAR represents a ballasted carrier moiety capable of releasing the diffusible yellow dye moiety or precursor thereof as a function of development;
(c) R represents hydrogen, an alkyl or substituted alkyl group of from 1 to about 12 carbon atoms, an aryl or substituted aryl group of from about 6 to about 12 carbon atoms, a substituted or unsubstituted 5- or 6-membered aromatic heterocyclic ring, or CAR, and
(d) n is 0, 1 or 2, with the proviso that when n is 0, then R is CAR.

24 Claims, No Drawings

PHOTOGRAPHIC PRODUCTS EMPLOYING NOVEL NONDIFFUSIBLE HYDRAZONE DYE-RELEASING COMPOUNDS

This invention relates to photography and more particularly to color diffusion transfer photography employing certain nondiffusible, hydrazone dye-releasing compounds which, as a function of development of a silver halide emulsion layer, release a diffusible yellow dye or precursor thereof. The dye-releasing compound can be premetallized or a metal complex of the released dye can be formed in an image-receiving layer.

Various formats for color, integral transfer elements are described in the prior art, such as U.S. Pat. Nos. 3,415,644; 3,415,645; 3,415,646; 3,647,437; 3,635,707; 3,756,815, and Canadian Patent Nos. 928,559 and 674,082. In these formats, the image-receiving layer containing the photographic image for viewing remains permanently attached and integral with the image generating and ancillary layers present in the structure when a transparent support is employed on the viewing side of the assemblage. The image is formed by dyes, produced in the image generating units, diffusing through the layers of the structure to the dye image-receiving layer. After exposure of the assemblage, an alkaline processing composition permeates the various layers to initiate development of the exposed photosensitive silver halide emulsion layers. The emulsion layers are developed in proportion to the extent of the respective exposures, and the image dyes which are formed or released in the respective image generating layers begin to diffuse throughout the structure. At least a portion of the imagewise distribution of diffusible dyes diffuses to the dye image-receiving layer to form an image of the original subject.

U.S. Pat. No. 3,953,211 of Imai et al relates to hydrazone dye developer compounds. The compounds of this invention are dye-releasing compounds and can be pre-metallized or post-metallized for greater stability to heat and light. There is no teaching in the Imai et al patent that their compounds can be premetallized or are metallizable.

U.S. Pat. Nos. 3,628,952 and 3,736,136 relate to compounds wherein a hydrazone moiety is part of a group from which a dye group is cleaved. Since the hydrazone moiety is not part of the dye group, it cannot be premet-allized or post-metallized, as are the compounds of the present invention.

Hydrazones have also been used in various analytical methods. In an article entitled "Preconcentration Of Trace Metals By Combined Complexation-Anion Exchange Part I. Cobalt, Zinc And Cadmium With 2-(3'-Sulphobenzoyl)-Pyridine-2-Pyridylhydrazone", *Analytica Chemica Acta*, 81 (1976), pp. 349–360 by Going, Wesenberg and Andrejat, reference is made to the formation of colored metal complexes of the named hydrazone. This disclosure relates only to certain analytical techniques, however, and is not related to photography.

It would be desirable to provide improved dye-releasing compounds containing chelating dye moieties, so that the dye which is released imagewise during processing, which can be premetallized or metallizable, can diffuse to an image-receiving layer to form a metal-complexed, dye transfer image having better hue, minimum unwanted absorption outside the blue region of the spectrum, narrower bandwidth, rapid diffusion rate and shorter access time than those of the prior art, as well as good stability to heat, light and chemical reagents.

A photographic element in accordance with the invention comprises a support having thereon at least one photosensitive silver halide emulsion layer having associated therewith a dye image-providing material comprising a nondiffusible compound capable of releasing at least one diffusible yellow dye moiety or precursor thereof having the formula:

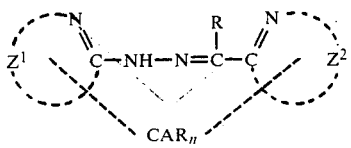

wherein:

(a) $Z^1$ and $Z^2$ each independently represents the atoms necessary to complete a 5- or 6-membered aromatic heterocyclic ring, such as, for example, a substituted or unsubstituted pyridine, quinoline, benzothiazole, pyrimidine or quinoxaline ring;

(b) CAR represents a ballasted carrier moiety capable of releasing the diffusible yellow dye moiety or precursor thereof as a function of development of the silver halide emulsion layer under alkaline conditions;

(c) R represents hydrogen, a substituted or unsubstituted alkyl group of from 1 to about 12 carbon atoms, such as, for example, methyl, ethyl, propyl, t-butyl, hexyl or decyl, any one of which may be substituted with various groups such as hydroxy, $SO_2NH_2$, $SO_2CH_3$, or $NHSO_2CH_3$; a substituted or unsubstituted aryl group of from about 6 to about 12 carbon atoms, such as, for example, phenyl, benzyl or phenethyl, any one of which may be substituted with various groups, such as hydroxy, $SO_2NH_2$, $SO_2CH_3$, or $NHSO_2CH_3$; a substituted or unsubstituted 5- or 6-membered aromatic heterocyclic ring, such as those listed above for $Z^1$ and $Z^2$; or CAR; and (d) n is 0, 1 or 2, with the proviso that when n is 0, then R is CAR.

Examples of groups which R may represent, other than hydrogen, include $CH_3$, $C_2H_5$, $t$-$C_4H_9$,

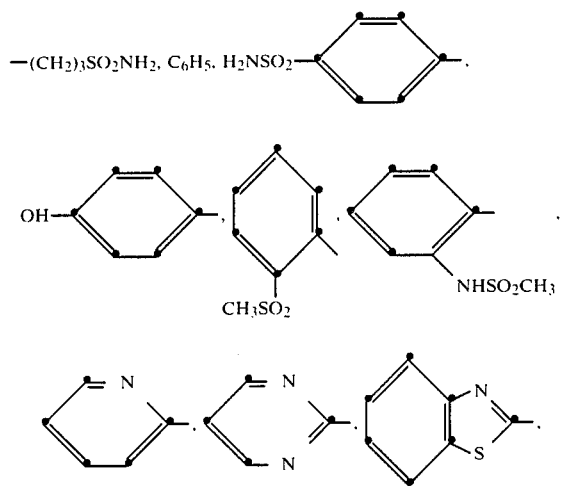

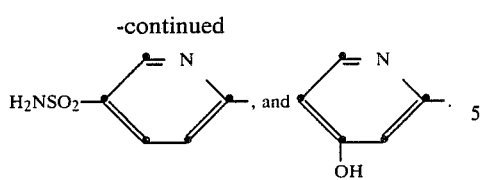, and 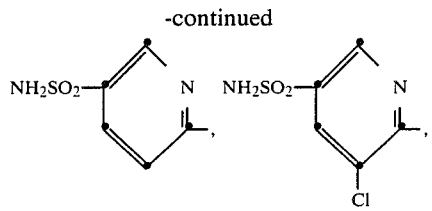

When R represents CAR, it may be, for example,

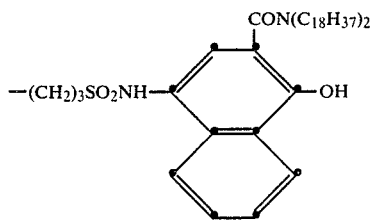

or

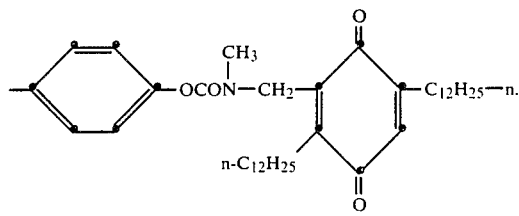

Examples of heterocyclic groups which $Z^1$ and $Z^2$ may represent include

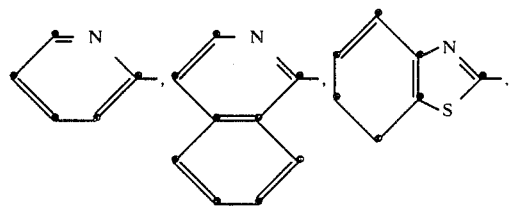

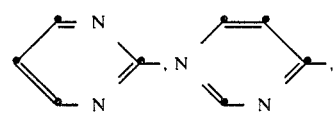

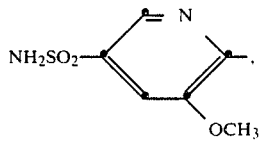

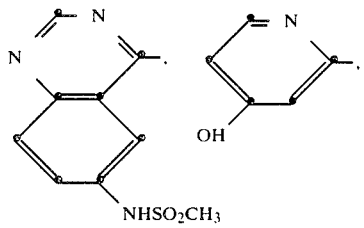

In a preferred embodiment of the invention, R represents hydrogen, methyl, ethyl, substituted propyl, butyl, phenyl, substituted phenyl, pyridine, substituted pyridine, pyrimidine or benzothiazole. In another preferred embodiment of the invention, $Z^1$ and $Z^2$ each independently represents the atoms necessary to complete a pyridine or substituted pyridine ring, R represents hydrogen, methyl, or pyridine, n is 1 and CAR is attached to the pyridine ring of $Z^1$.

In another embodiment of the invention, CAR may have attached thereto two dye moieties, as shown by the formula above, in which case two dye moieties will be released from one CAR moiety.

Other substituents may also be present in the two rings illustrated above, such as alkyl of 1 to 6 carbon atoms, acyl, aryl of 6 to 10 carbon atoms, aralkyl, alkylsulfonyl, amino, alkoxy, halogens such as chloro or bromo, morpholino, phenylsulfamoyl, solubilizing groups such as sulfonamido, sulfamoyl, carboxy, sulfo or hydrolyzable precursors thereof.

In another preferred embodiment of our invention, the dye image-providing materials described above may be premetallized, i.e., they would comprise a coordination complex of the nondiffusible compounds described above and a polyvalent metal ion. Such metal ions include, for example, zinc(II), nickel(II), copper(II), cobalt(II) and cobalt(III) ions. Especially good results are obtained with nickel(II) ions.

There is great latitude in selecting a CAR moiety which is attached to the dye-releasing compounds described above. Depending upon the nature of the ballasted carrier selected, various groups may be needed to attach or link the carrier moiety to the dye. Such linking groups are considered to be a part of the CAR moiety in the above definition. It should also be noted that, when the dye moiety is released from the compound, cleavage may take place in such a position that part or all of the linking group, if one is present, and even part of the ballasted moiety, may be transferred to the image-receiving layer, along with the dye moiety. In any event, the dye nucleus as shown above can be thought of as the minimum which is transferred.

CAR moieties useful in the invention are described in U.S. Pat. Nos. 3,227,550; 3,628,952; 3,227,552 and 3,844,785 (dye released by chromogenic coupling); U.S. Pat. Nos. 3,443,939 and 3,443,940 (dye released by intramolecular ring closure); U.S. Pat. Nos. 3,698,897 and 3,725,062 (dye released from hydroquinone derivatives); U.S. Pat. No. 3,728,113 (dye released from a hydroquinonylmethyl quaternary salt); U.S. Pat. Nos. 3,719,489 and 3,443,941 (silver ion induced dye release); British Patent Publication No. 2,017,950A (dye released by a dye bleach process); U.S. Pat. Nos. 4,053,312; 4,198,235; 4,179,231; 4,055,428 and 4,149,892 (dye released by oxidation and deamidation); and U.S. Pat. Nos. 3,245,789 and 3,980,497; Canadian Patent No. 602,607; British Patent No. 1,464,104; Research Disclosure 14447, April 1976; U.S. Pat. No. 4,139,379 of Chasman et al, U.S. Pat. No. 4,232,107 and European Patent Publication No. 12908 (dye released by miscellaneous mechanisms), the disclosures of which are hereby incorporated by reference.

In a further preferred embodiment of the invention, the ballasted carrier moiety or CAR as described above may be represented by the following formula:

(Ballast-Carrier-Link)- wherein:

(a) Ballast is an organic ballasting radical of such molecular size and configuration as to render said compound nondiffusible in said photographic element during development in an alkaline processing composition;

(b) Carrier is an oxidizable acyclic, carbocyclic or heterocyclic moiety (see "The Theory of the Photographic Process", by C. E. K. Mees and T. H. James, Third Edition, 1966, pages 282 to 283), e.g., moieties containing atoms according to the following configuration:

a(—C=C)$_b$— wherein:

b is a positive integer of 1 to 2; and a represents the radicals OH, SH, NH or hydrolyzable precursors thereof; and (c) Link represents a group which, upon oxidation of said Carrier moiety, is capable of being hydrolytically cleaved to release the diffusible azo dye. For example, Link may be the following groups:

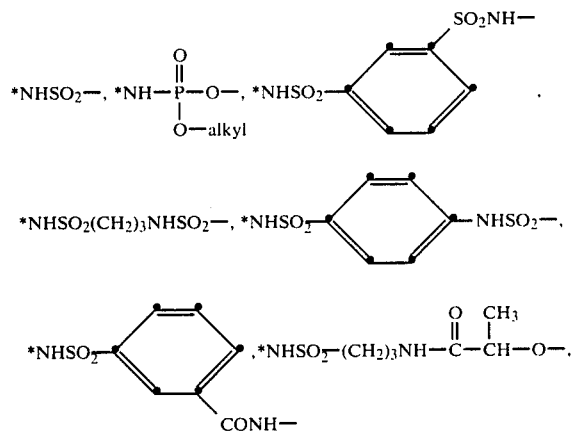

wherein * represents the position of attachment to Carrier. *

The Ballast group in the above formula is not critical, so long as it confers nondiffusibility to the compound. Typical Ballast groups include long-chain alkyl radicals, as well as aromatic radicals of the benzene and naphthalene series linked to the compound. Useful Ballast groups generally have at least 8 carbon compounds, such as substituted or unsubstituted alkyl groups of 8 to 22 carbon atoms; a carbamoyl radical having 8 to 30 carbon atoms, such as —CONH(CH$_2$)$_4$—O—C$_6$H$_3$(C$_5$H$_{11}$)$_2$ or —CON(C$_{12}$H$_{25}$)$_2$; or a keto radical having 8 to 30 carbon atoms, such as —CO—C$_{17}$H$_{35}$ or —CO—C$_6$H$_4$(t—C$_{12}$H$_{25}$).

For specific examples of Ballast-Carrier moieties useful as the CAR moiety in this invention, reference is made to the November 1976 edition of Research Disclosure, pages 68 through 74, and the April 1977 edition of Research Disclosure, pages 32 through 39, the disclosures of which are hereby incorporated by reference.

In a highly preferred embodiment of the invention, the ballasted carrier moiety or CAR in the above formula is a group having the formula:

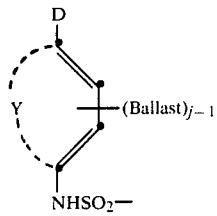

wherein:

(a) Ballast is an organic ballasting radical of such molecular size and configuration (e.g., simple organic groups or polymeric groups) as to render said compound nondiffusible in a photographic element during development in an alkaline processing composition;

(b) D is OR$^1$ or NHR$^2$ wherein R$^1$ is hydrogen or a hydrolyzable moiety, such as acetyl, mono-, di- or trichloroacetyl radicals, perfluoroacyl, pyruvyl, alkoxyacyl, nitrobenzoyl, cyanobenzoyl, sulfonyl or sulfinyl, and R$^2$ is hydrogen or a substituted or unsubstituted alkyl group of 1 to 22 carbon atoms, such as methyl, ethyl, hydroxyethyl, propyl, butyl, secondary butyl, tertbutyl, cyclopropyl, 4-chlorobutyl, cyclobutyl, 4-nitroamyl, hexyl, cyclohexyl, octyl, decyl, octadecyl, dodecyl, benzyl or phenethyl (when R$^2$ is an alkyl group of greater than 8 carbon atoms, it can serve as a partial or sole Ballast);

(c) Y represents at least the atoms necessary to complete a benzene nucleus, a naphthalene nucleus, or a 5 to 7 membered heterocyclic ring, such as pyrazolone or pyrimidine; and (d) j is a positive integer of 1 to 2 and is 2 when D is OR$^1$ or when R$^2$ is hydrogen or an alkyl group of less than 8 carbon atoms.

Especially good results are obtained in the above formula when D is OH, j is 2, and Y is a naphthalene nucleus.

Examples of the CAR moiety in this highly preferred embodiment are disclosed in U.S. Pat. Nos. 4,076,529; 3,993,638 and 3,928,312, the disclosures of which are hereby incorporated by reference, and include the following:

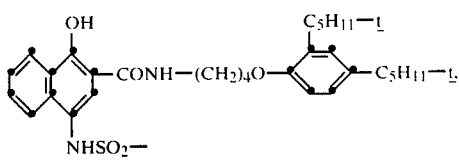

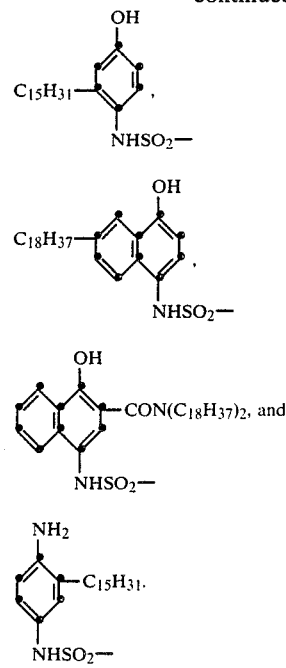

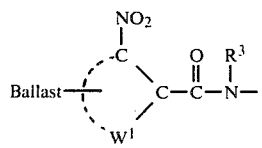

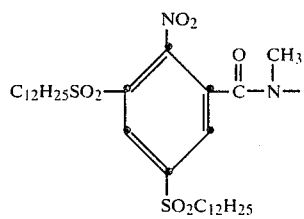

In another highly preferred embodiment of the invention, the ballasted carrier moiety or CAR in the above formulas is such that the diffusible azo dye is released as an inverse function of development of the silver halide emulsion layer under alkaline conditions. This is ordinarily referred to as positive-working dye-release chemistry. In one of these embodiments, the ballasted carrier moiety or CAR in the above formulas may be a group having the formula:

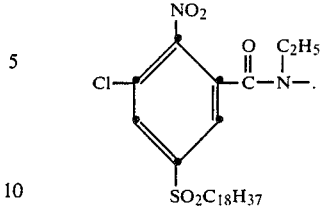
(I)

wherein:

Ballast is an organic ballasting radical of such molecular size and configuration as to render said compound nondiffusible in a photographic element during development in an alkaline processing composition;

$W^1$ represents at least the atoms necessary to complete a benzene nucleus (including various substituents thereon); and $R^3$ is an alkyl (including substituted alkyl) radical having 1 to about 4 carbon atoms.

Examples of the CAR moiety in this formula (I) include the following:

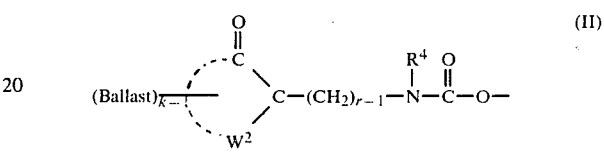

and

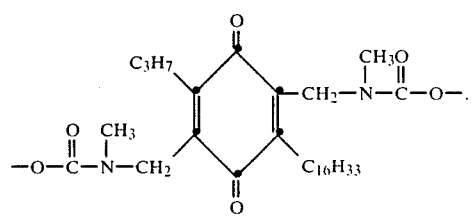

In a second embodiment of positive-working dye-release chemistry as referred to above, the ballasted carrier moiety or CAR in the above formulas may be a group having the formula:

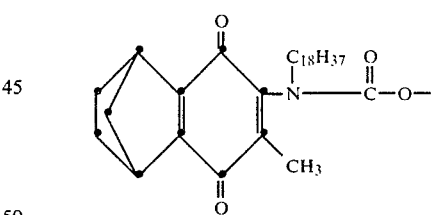
(II)

wherein:

Ballast is an organic ballasting radical of such molecular size and configuration as to render said compound nondiffusible in a photographic element during development in an alkaline processing composition;

$W^2$ represents at least the atoms necessary to complete a quinone nucleus (including various substituents thereon);

r is a positive integer of 1 or 2;

$R^4$ is an alkyl (including substituted alkyl) radical having 1 to about 40 carbon atoms or an aryl (including substituted aryl) radical having 6 to about 40 carbon atoms; and k is a positive integer of 1 to 2 and is 2 when $R^4$ is a radical of less than 8 carbon atoms.

Examples of the CAR moiety in this formula (II) include the following:

In using the compounds in formulas I and II above, they are employed in a photographic element similar to the other nondiffusible dye-releasers described previously. Upon reduction of the compound as a function of silver halide development under alkaline conditions, the metallizable azo dye is released. In this embodiment, conventional negative-working silver halide emulsions, as well as direct-positive emulsions, can be employed. For further details concerning these particular CAR moieties, including synthesis details, reference is made to U.S. Pat. No. 4,139,379 of Chasman et al, the disclosure of which is hereby incorporated by reference.

In a third embodiment of positive-working dye-release chemistry as referred to above, the ballasted carrier moiety or CAR in the above formulas may be a group having the formula:

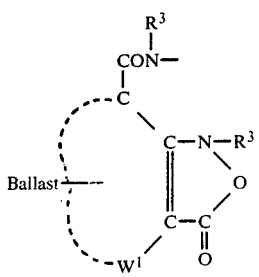
(III)

wherein: Ballast, $W^1$ and $R^3$ are as defined for formula (1) above.

Examples of the CAR moiety in this formula (III) include the following:

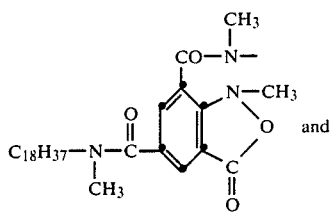

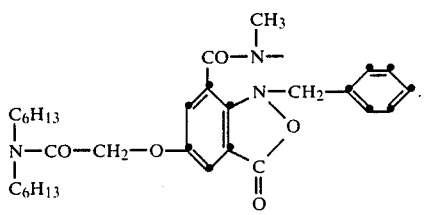

For further details concerning this particular CAR moiety, including synthesis details, reference is made to U.S. Pat. No. 4,199,354 of Hinshaw et al, the disclosure of which is hereby incorporated by reference.

In a fourth embodiment of positive-working dye-release chemistry as referred to above, the ballasted carrier moiety or CAR in the above formulas may be a group having the formula:

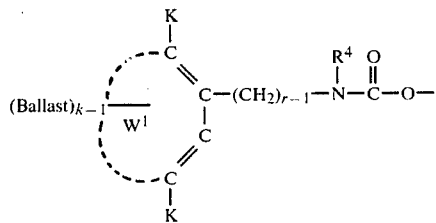
(IV)

wherein:
Ballast, r, $R^4$ and k are as defined for formula (II) above;
$W^1$ is as defined for formula (I) above; and K is OH or a hydrolyzable precursor thereof.

Examples of the CAR moiety in this formula (IV) include the following:

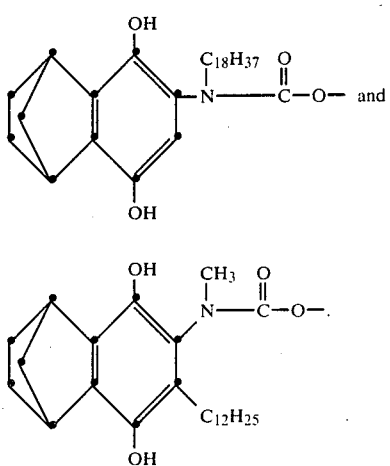

For further details concerning this particular CAR moiety, including synthesis details, reference is made to U.S. Pat. No. 3,980,479 of Fields et al, the disclosure of which is hereby incorporated by reference.

Representative compounds included within the scope of the invention include the following:

Metallizable Compounds

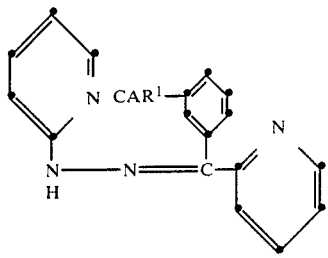
(1)

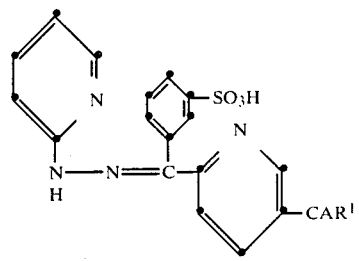
(2)

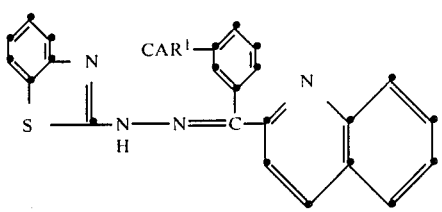
(3)

-continued
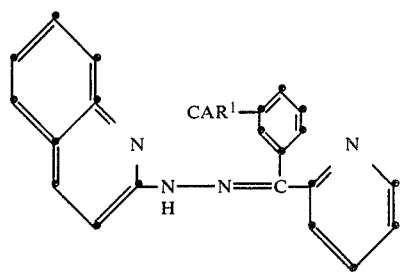 (4)
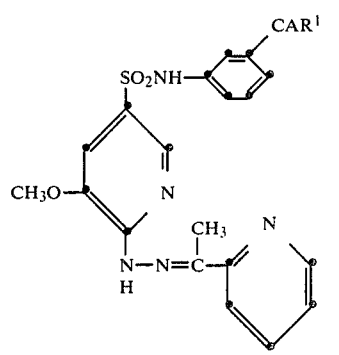 (5)
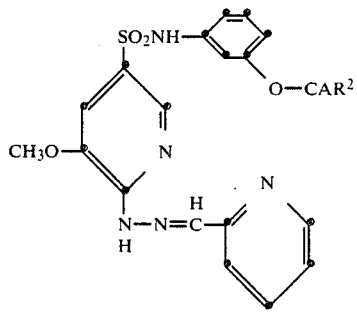 (6)
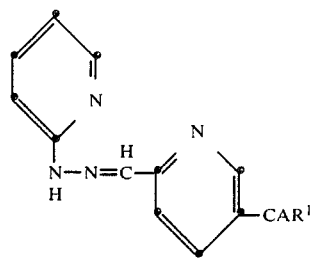 (7)
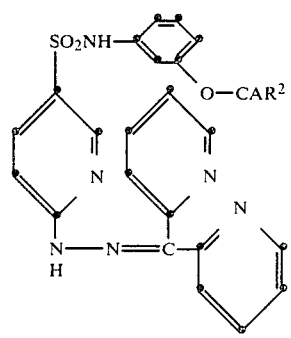 (8)
-continued
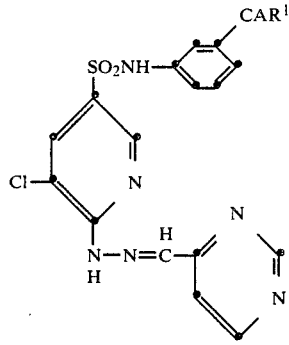 (9)
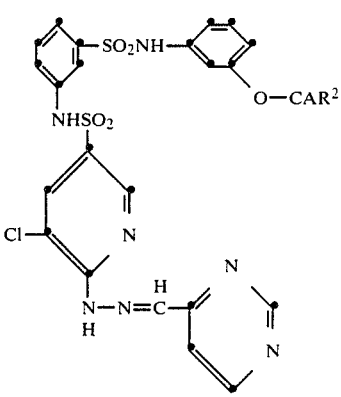 (10)
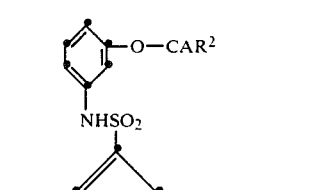 (11)
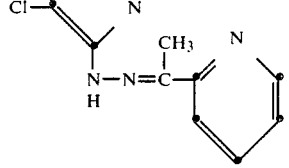 (11)
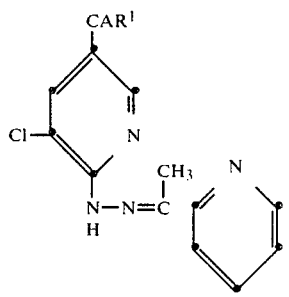 (12)
Premetallized Compounds

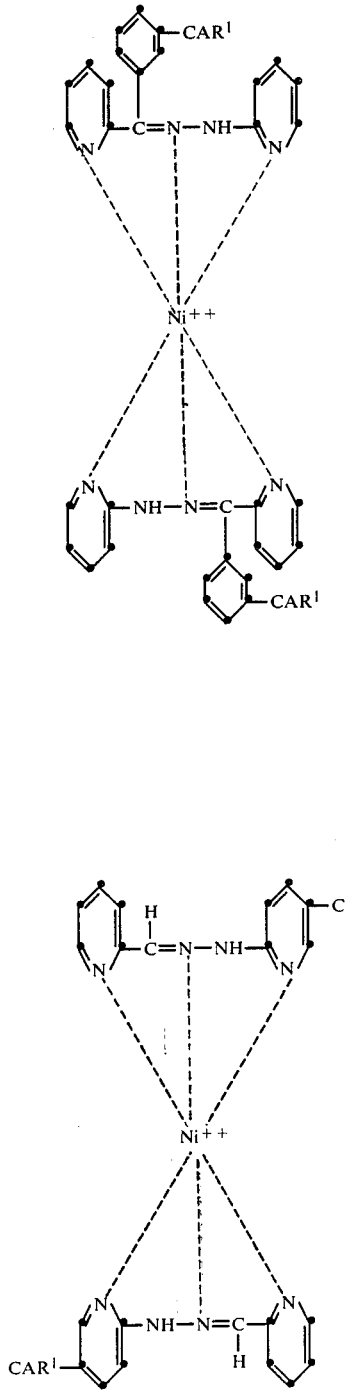

(13)

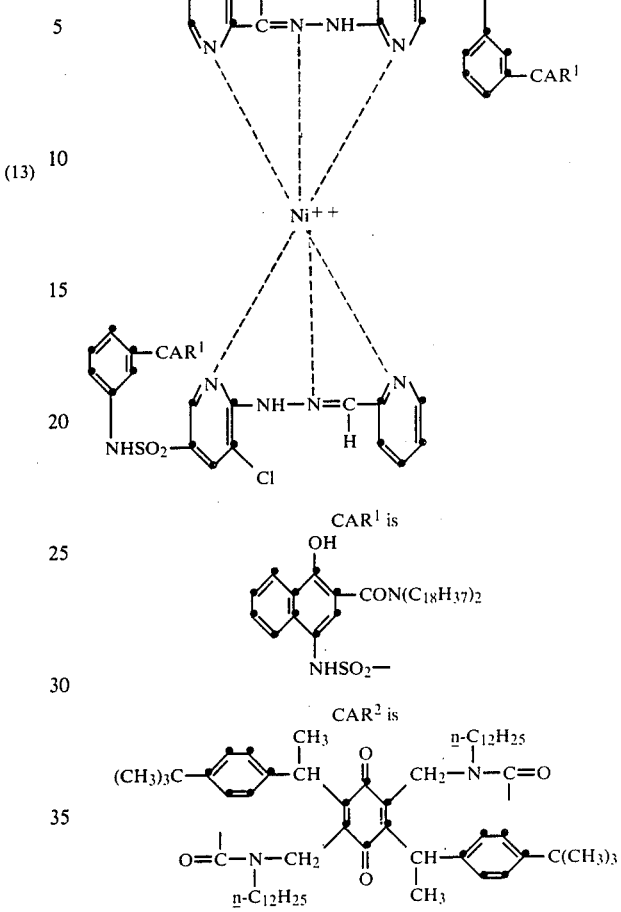

(14)

(15)

The general procedures for preparing compounds according to the invention are known to those skilled in the art.

A process for producing a photographic transfer image in color according to the invention comprises:

(a) treating an imagewise-exposed photographic element as described above having a metallizable dye-releasing compound with an alkaline processing composition in the presence of a silver halide developing agent to effect development of each of the exposed silver halide emulsion layers;

(b) the dye-releasing compound then releasing the diffusible dye as described above imagewise as a function of the development of each of the silver halide emulsion layers;

(c) at least a portion of the imagewise distribution of the dye diffusing to a dye image-receiving layer; and (d) contacting the imagewise distribution of dye with metal ions, thereby forming a metal-complexed yellow dye transfer image.

The dye moiety which is released from the metallizable dye-releasing compounds described above is an essentially colorless tridentate ligand but will form a yellow coordination complex in the image-receiving layer with polyvalent metal ions. The metal ions can be present in the image-receiving layer itself or in a layer adjacent thereto, or the image-receiving layer can be contacted with metal ions in a bath after diffusion of the dye has taken place. Metal ions most useful in the invention are those which are essentially colorless when incorporated into the image-receiving element, are inert with respect to the silver halide layers, react readily with the released dye to form a complex of the desired hue, are tightly coordinated to the dye in the complex, have a stable oxidation state, and form a dye complex which is stable to heat, light and chemical reagents. In general, good results are obtained with polyvalent metal ions such as copper (II), zinc (II), nickel (II), platinum (II), palladium (II), cobalt (II) and cobalt (III) ions. The metal ions may be provided by a salt or complex of the metal, for example $Ni(NH_3)_6SO_4$, $Cu(NH_3)_6SO_4$, nickel sulfate, nickel ethanolamine, diethanolamine or triethanolamine complexes; and other complexes of nickel(II) and copper(II) containing basic ligands, for example, a polyvinylpyridine-nickel complex.

It is believed that the coordination complex which is formed from the tridentate, metallizable dye ligand according to the invention in one of the preferred embodiments thereof has the following structure:

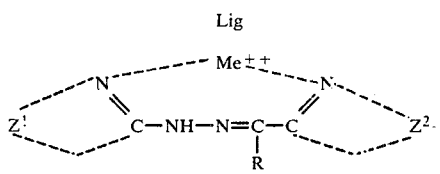

wherein:
$Z^1$, $Z^2$ and R are defined as above;
Me is metal; and
Lig is one or more ligand groups, depending upon the coordination number of the metal ion, such as $H_2O$, Cl or pyridine, a second dye moiety or a part of a polymer. (A divalent metal ion in solution always has a number of ligand groups attached to it depending upon its coordination number and the relative reactivity of various ligand groups such as water, ammonia, chloride, pyridine or acetate, which may be in the solution environment of the metal ion. These ligands can be displaced by a tridentate dye ligand which would form a more stable complex.)

Thus, in accordance with this preferred embodiment of the invention, a photographic element is provided which comprises a support having thereon a coordination complex of a polyvalent metal ion and a compound having the formula:

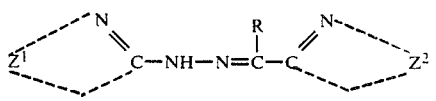

wherein $Z^1$, $Z^2$ and R are defined as above.

The element usually contains a photographic mordant or image-receiving layer to bind the dye or coordination complex thereto.

The structures shown above may also, of course, be substituted in the same manner as described above for the starting compounds from which they are released.

It will be appreciated that, after processing the photographic element described above, there remains in it after transfer has taken place an imagewise distribution of dye in addition to developed silver. A color image comprising residual nondiffusible compound is obtained in this element if the residual silver and silver halide are removed by any conventional manner well known to those skilled in the photographic art, such as a bleach bath, followed by a fix bath, a bleach-fix bath, etc. The imagewise distribution of dye may also diffuse out of the element into these baths, if desired, rather than to an image-receiving element. If a negative-working silver halide emulsion is employed in certain preferred photosensitive elements, described above, then a positive color image, such as a reflection print, a color transparency or motion picture film, is produced in this manner. If a direct-positive silver halide emulsion is employed in such photosensitive elements, then a negative color image is produced.

The photographic element in the above-described process is treated in any manner with an alkaline processing composition to effect or initiate development. A preferred method for applying processing composition is by use of a rupturable container or pod which contains the composition. In general, the processing composition employed in this invention contains the developing agent for development, although the composition could also just be an alkaline solution where the developer is incorporated in the photographic element, image-receiving element or process sheet, in which case the alkaline solution serves to activate the incorporated developer.

A photographic film unit or assemblage in accordance with this invention comprises:
(1) a photographic element as described above,
(2) a dye image-receiving layer, and
(3) an alkaline processing composition and means containing same for discharge within the assemblage, the assemblage containing a silver halide developing agent.

The alkaline processing composition can be contained, for example, in a rupturable container which is adapted to be positioned during processing of the film unit so that a compressive force applied to the container by pressure-applying members, such as would be found in a camera designed for in-camera processing, will effect a discharge of the container's contents within the film unit.

In the embodiment described above, the dye image-receiving layer may itself contain metal ions or the metal ions may be present in an adjacent layer, so that the tridentate, metallizable dye ligand which is released will form a coordination complex therewith. The dye thus becomes immobilized in the dye image-receiving layer and metallized at the same time. Alternatively, the dye image in the dye image-receiving layer may be treated with a solution containing metal ions to effect metallization. The formation of the coordination complex shifts the absorption of the dye to the desired hue, usually to a longer wavelength, which has a different absorption than that of the initial dye-releasing compound. If this shift is large enough, then the dye-releasing compound may be incorporated in a silver halide emulsion layer without adversely affecting its sensitivity.

The dye image-receiving layer in the above-described film assemblage is optionally located on a separate support adapted to be superposed on the photographic element after exposure thereof. Such image-receiving elements are generally disclosed, for example, in U.S. Pat. No. 3,362,819. When the means for discharging the processing composition is a rupturable container, it is usually positioned in relation to the photographic element and the image-receiving element so that a compressive force applied to the container by pressure-applying members, such as would be found in a typical camera used for in-camera processing, will effect a discharge of the container's contents between the image-receiving element and the outermost layer of the photographic element. After processing, the dye image-receiving element is separated from the photographic element.

The dye image-receiving layer in the above-described film assemblage in another embodiment is located integrally with the photographic element between the support and the lowermost photosensitive silver halide emulsion layer. One useful format for integral receiver-negative photographic elements is disclosed in Belgian Patent No. 757,960. In such an embodiment, the support for the photographic element is transparent and is coated with an image-receiving layer, a substantially opaque light-reflective layer, e.g., $TiO_2$, and then the photosensitive layer or layers described above. After exposure of the photographic element, a rupturable container containing an alkaline processing composition and an opaque process sheet are brought into superposed position. Pressure-applying members in the camera rupture the container and spread processing composition over the photographic element as the film unit is withdrawn from the camera. The processing composition develops each exposed silver halide emulsion layer and dye images are formed as a function of development which diffuse to the image-receiving layer to provide a positive, right-reading image which is viewed through the transparent support on the opaque reflecting layer background. For other details concerning the format of this particular integral film unit, reference is made to the above-mentioned Belgian Patent No. 757,960.

Another format for integral negative-receiver photographic elements in which the present invention is useful is disclosed in Canadian Patent No. 928,559. In this embodiment, the support for the photographic element is transparent and is coated with the image-receiving layer, a substantially opaque, light-reflective layer and the photosensitive layer or layers described above. A rupturable container containing an alkaline processing composition and an opacifier is positioned adjacent the top layer and a transparent top sheet which has thereon a neutralizing layer and a timing layer. The film unit is placed in a camera, exposed through the transparent top sheet and then passed through a pair of pressure-applying members in the camera as it is being removed therefrom. The pressure-applying members rupture the container and spread processing composition and opacifier over the negative portion of the film unit to render it light-insensitive. The processing composition develops each silver halide layer and dye images are formed as a result of development which diffuse to the image-receiving layer to provide a positive, right-reading image which is viewed through the transparent support on the opaque reflecting layer background. For further details concerning the format of this particular integral film unit, reference is made to the abovementioned Canadian Patent No. 928,559.

Still other useful integral formats in which this invention can be employed are described in U.S. Pat. Nos. 3,415,644; 3,415,645; 3,415,646; 3,647,437 and 3,635,707. In most of these formats, a photosensitive silver halide emulsion is coated on an opaque support and a dye image-receiving layer is located on a separate transparent support superposed over the layer outermost from the opaque support. In addition, this transparent support also preferably contains a neutralizing layer and a timing layer underneath the dye image-receiving layer.

Another embodiment of the invention uses the image-reversing technique disclosed in British Patent No. 904,364, page 19, lines 1 through 41. In this process, the dye-releasing compounds are used in combination with physical development nuclei in a nuclei layer contiguous to the photosensitive silver halide emulsion layer. The film unit contains a silver halide solvent, preferably in a rupturable container with the alkaline processing composition.

The film unit or assembly used in the present invention is used to produce positive images in single- or multicolors. In a three-color system, each silver halide emulsion layer of the film assembly will have associated therewith a dye-releasing compound which releases a dye possessing a predominant spectral absorption within the region of the visible spectrum to which said silver halide emulsion is sensitive (initially or after forming the coordination complex), i.e., the blue-sensitive silver halide emulsion layer will have the yellow or yellow-forming dye-releaser of the invention associated therewith, the green-sensitive silver halide emulsion layer will have a magenta or magenta-forming dye-releaser associated therewith, and the red-sensitive silver halide emulsion layer will have a cyan or cyan-forming dye-releaser associated therewith. The dye-releaser associated with each silver halide emulsion layer is contained either in the silver halide emulsion layer itself or in a layer contiguous to the silver halide emulsion layer.

The concentration of the dye-releasing compounds that are employed in the present invention may be varied over a wide range, depending upon the particular compound employed and the results which are desired. For example, the dye-releasers of the present invention may be coated in layers by using coating solutions containing between about 0.5 and about 8 percent by weight of the dye-releaser distributed in a hydrophilic film-forming natural material or synthetic polymer, such as gelatin, polyvinyl alcohol, etc, which is adapted to be permeated by aqueous alkaline processing composition.

Depending upon which CAR is used in the present invention, a variety of silver halide developing agents or electron transfer agents (ETA's) are useful in this invention. In certain embodiments of the invention, any ETA can be employed as long as it cross-oxidizes with the dye-releasers described herein. The ETA may also be incorporated in the photosensitive element to be activated by the alkaline processing composition. Specific examples of ETA's useful in this invention include hydroquinone compounds, aminophenol compounds, catechol compounds, and phenylenediamine compounds. In highly preferred embodiments, the ETA. is a 3-pyrazolidinone compound. A combination of different ETA's, such as those disclosed in U.S. Pat. No. 3,039,869, can also be employed. These ETA's are employed in the liquid processing composition or contained, at least in part, in any layer or layers of the photographic element or film unit to be activated by the alkaline processing composition, such as in the silver halide emulsion layers, the dye image-providing material layers, interlayers, image-receiving layer, etc.

In a preferred embodiment of the invention, the silver halide developer or ETA employed in the process becomes oxidized upon development and reduces silver halide to silver metal. The oxidized developer than cross-oxidizes the dye-releasing compound. The product of cross-oxidation then undergoes alkaline hydrolysis, thus releasing an imagewise distribution of diffusible dye which then diffuses to the receiving layer to provide the dye image. The diffusible moiety is transferable in alkaline processing composition either by virtue of its self-diffusivity or by its having attached to it one or more solubilizing groups, for example, a carboxy, sulpho, sulphonamido, hydroxy or morpholino group.

In using the dye-releasing compounds according to the invention which produce diffusible dye images as a function of development, either conventional negative-working or direct-positive silver halide emulsions are employed. If the silver halide emulsion employed is a direct-positive silver halide emulsion, such as an internal-image emulsion designed for use in the internal image reversal process or a fogged, direct-positive emulsion such as a solarizing emulsion, which is developable in unexposed areas, a positive image can be obtained in certain embodiments on the dye image-receiving layer. After exposure of the film unit, the alkaline processing composition permeates the various layers to initiate development of the exposed photosensitive silver halide emulsion layers. The developing agent present in the film unit develops each of the silver halide emulsion layers in the unexposed areas (since the silver halide emulsions are direct-positive ones), thus causing the developing agent to become oxidized imagewise corresponding to the unexposed areas of the direct-positive silver halide emulsion layers. The oxidized developing agent then crossoxidizes the dye-releasing compounds and the oxidized form of the compounds then undergoes a base-catalyzed reaction to release the dyes imagewise as a function of the imagewise exposure of each of the silver halide emulsion layers. At least a portion of the imagewise distributions of diffusible dyes diffuse to the image-receiving layer to form a positive image of the original subject. After being contacted by the alkaline processing composition, a neutralizing layer in the film unit or image-receiving unit lowers the pH of the film unit or image receiver to stabilize the image.

Internal-image silver halide emulsions useful in this invention are described more fully in the November 1976 edition of *Research Disclosure*, pages 76 through 79, the disclosure of which is hereby incorporated by reference.

The various silver halide emulsion layers of a color film assembly employed in this invention are disposed in the usual order, i.e., the blue-sensitive silver halide emulsion layer first with respect to the exposure side, followed by the green-sensitive and red-sensitive silver halide emulsion layers. If desired, a yellow dye layer or a yellow colloidal silver layer can be present between the blue-sensitive and green-sensitive silver halide emulsion layers for absorbing or filtering blue radiation that is transmitted through the blue-sensitive layer. If desired, the selectively sensitized silver halide emulsion layers can be disposed in a different order, e.g., the blue-sensitive layer first with respect to the exposure side, followed by the red-sensitive and green-sensitive layers.

The rupturable container employed in certain embodiments of this invention is disclosed in U.S. Pat. Nos. 2,543,181; 2,643,886; 3,653,732; 2,723,051; 3,056,492; 3,056,491 and 3,152,515. In general, such containers comprise a rectangular sheet of fluid-and air-impervious material folded longitudinally upon itself to form two walls which are sealed to one another along their longitudinal and end margins to form a cavity in which processing solution is contained.

Generally speaking, except where noted otherwise, the silver halide emulsion layers employed in the invention comprise photosensitive silver halide dispersed in gelatin and are about 0.6 to 6 microns in thickness; the dye-releasers are dispersed in an aqueous alkaline solution-permeable polymeric binder, such as gelatin, as a separate layer about 0.2 to 7 microns in thickness; and the alkaline solution-permeable polymeric interlayers, e.g, gelatin, are about 0.2 to 5 microns in thickness. Of course, these thicknesses are approximate only and can be modified according to the product desired.

Scavengers for oxidized developing agent can be employed in various interlayers of the photographic elements of the invention. Suitable materials are disclosed on page 83 of the November 1976 edition of *Research Disclosure*, the disclosure of which is hereby incorporated by reference.

Any material is useful as the image-receiving layer in this invention as long as the desired function of mordanting or otherwise fixing the dye images is obtained. The particular material chosen will, of course, depend upon the dye to be mordanted. Suitable materials are disclosed on pages 80 through 82 of the November 1976 edition of *Research Disclosure*, the disclosure of which is hereby incorporated by reference.

Use of a neutralizing material in the film units employed in this invention will usually increase the stability of the transferred image. Generally, the neutralizing material will effect a reduction in the pH of the image layer from about 13 or 14 to at least 11 and preferably 5 to 8 within a short time after imbibition. Suitable materials and their functioning are disclosed on pages 22 and 23 of the July 1974 edition of *Research Disclosure*, and pages 35 through 37 of the July 1975 edition of *Research Disclosure*, the disclosures of which are hereby incorporated by reference.

A timing or inert spacer layer can be employed in the practice of this invention over the neutralizing layer which "times" or controls the pH reduction as a function of the rate at which alkali diffuses through the inert spacer layer. Examples of such timing layers and their functioning are disclosed in the *Research Disclosure* articles mentioned in the paragraph above concerning neutralizing layers.

The alkaline processing composition employed in this invention is the conventional aqueous solution of an alkaline material, e.g., alkali metal hydroxides or carbonates such as sodium hydroxide, sodium carbonate or an amine such as diethylamine, preferably possessing a pH in excess of 11, and preferably containing a developing agent as described previously. Suitable materials and addenda frequently added to such compositions are disclosed on pages 79 and 80 of the November 1976 edition of *Research Disclosure*, the disclosure of which is hereby incorporated by reference.

The alkaline solution-permeable, substantially opaque, light-reflective layer employed in certain embodiments of photographic film units used in this invention is described more fully in the November 1976 edition of *Research Disclosure*, page 82, the disclosure of which is hereby incorporated by reference.

The supports for the photographic elements used in this invention can be any material as long as it does not deleteriously affect the photographic properties of the film unit and is dimensionally stable. Typical flexible sheet materials are described on page 85 of the November 1976 edition of *Research Disclosure,* the disclosure of which is hereby incorporated by reference.

While the invention has been described with reference to layers of silver halide emulsions and dye image-providing materials, dotwise coating, such as would be obtained using a gravure printing technique, could also be employed. In this technique, small dots of blue-, green- and red-sensitive emulsions have associated therewith, respectively, dots of yellow, magenta and cyan color-providing substances. After development, the transferred dyes would tend to fuse together into a continuous tone. In an alternative embodiment, the emulsions sensitive to each of the three primary regions of the spectrum can be disposed as a single segmented layer, e.g., as by the use of microvessels, as described in Whitmore U.S. Pat. No. 4,362,806, issued Dec. 7, 1982.

The silver halide emulsions useful in this invention, both negative-working and direct-positive ones, are well known to those skilled in the art and are described in *Research Disclosure,* Volume 176, December 1978, Item No. 17643, pages 22 and 23, "Emulsion preparation and types"; they are usually chemically and spectrally sensitized as described on page 23, "Chemical sensitization", and "Spectral sensitization and desensitization", of the above article; they are optionally protected against the production of fog and stabilized against loss of sensitivity during keeping by employing the materials described on pages 24 and 25, "Antifoggants and stabilizers", of the above article; they usually contain hardeners and coating aids as described on page 26, "Hardeners", and pages 26 and 27, "Coating aids", of the above article; they and other layers in the photographic elements used in this invention usually contain plasticizers, vehicles and filter dyes described on page 27, "Plasticizers and lubricants"; page 26, "Vehicles and vehicle extenders"; and pages 25 and 26, "Absorbing and scattering materials", of the above article; they and other layers in the photographic elements used in this invention can contain addenda which are incorporated by using the procedures described on page 27, "Methods of addition", of the above article; and they are usually coated and dried by using the various techniques described on pages 27 and 28, "Coating and drying procedures", of the above article, the disclosures of which are hereby incorporated by reference.

The term "nondiffusing" used herein has the meaning commonly applied to the term in photography and denotes materials that, for all practical purposes, do not migrate or wander through organic colloid layers, such as gelatin, in the photographic elements of the invention in an alkaline medium and preferably when processed in a medium having a pH of 11 or greater. The same meaning is to be attached to the term "immobile". The term "diffusible" as applied to the materials of this invention has the converse meaning and denotes materials having the property of diffusing effectively through the colloid layers of the photographic elements in an alkaline medium. "Mobile" has the same meaning as "diffusible."

The term "associated therewith" as used herein is intended to mean that the materials can be in either the same or different layers, so long as the materials are accessible to one another.

The following examples are provided to further illustrate the invention.

EXAMPLE 1

Synthesis of Compound 11 (Positive Redox Dye-Releaser)

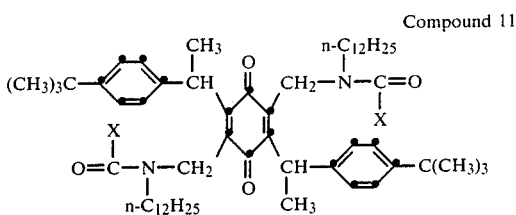

Compound 11

X is

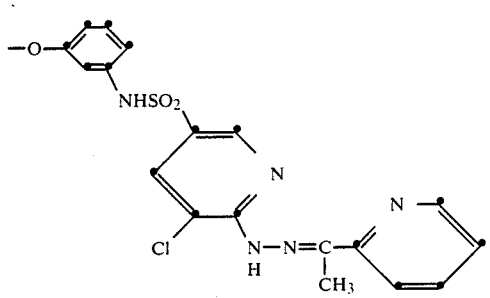

The dye portion of Compound 11 (5.0 g, 12 mmol) was dissolved in dry pyridine (150 ml) and triethylamine (1.22 g) was added, followed by 3,6-bis(1-p-t-butylphenylethyl)-2,5-bis(N-n-dodecylchloroformamidomethyl)benzoquinone (5.7 g, 6 mmol) (see U.S. Pat. No. 4,204,870, column 31). The mixture was stirred for 72 hours, then poured onto ice (1200 ml). Concentrated HCl was added to bring the pH to 5, and the mixture was filtered, the precipitate washed with water and dried by suction. The crude product was extracted into hot methanol, filtered hot, and reprecipitaed from the cooled filtrate, 6.3 g of material obtained. This was purified by chromatography on silica gel, eluting with increasing amounts of ethyl acetate in dichloromethane. A middle fraction contained the desired product, 2.4 g.

Intermediates

Preparation of: Dye Portion of Compound 11

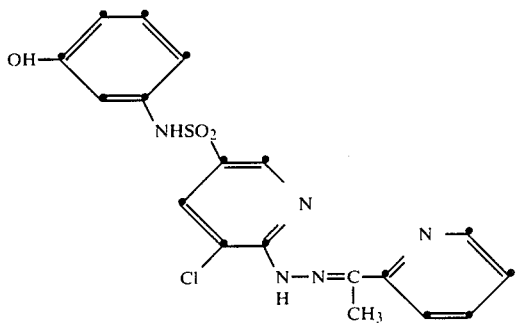

5-Chloro-6-hydrazino-3'-hydroxy-3-pyridinesulfonanilide (9.45 g, 30 mmol) was dissolved in 400 ml of 50 percent aqueous ethanol containing 5 ml conc. HCl, the solution being warmed as necessary to effect solution. 2-Acetylpyridine (4 g, 33 mmol) was then added; and stirring was continued for 5 minutes. A solution of sodium acetate (10 g) in 60 ml water was added dropwise over 10 minutes; and the solution was warmed for an additional 30 minutes. The precipitated product was filtered from the cooled solution, washed with water, and dried by suction. Yield: 11.6 g, 93 percent.

Preparation of:
5-Chloro-6-hydrazino-3'-hydroxy-3-pyridinesulfonanilide

To 500 ml ethanol was added 5,6-dichloro-3'-hydroxy-3-pyridinesulfonanilide (10.4 g, 42 mmol) and 95 percent hydrazine (60 mmol). The reaction mixture was refluxed overnight. The completely reacted mixture was chilled, and the precipitate was filtered off and washed with ethanol. The filtrate was concentrated so as to obtain a second crop, yielding a total of 16.5 g. The solid was stirred in 250 ml of water to remove any salts. The product was filtered, washed with water, and dried under vacuum at 50° C. to give 10.61 g (80 percent) of pure product.

Preparation of:
5,6-Dichloro-3'-hydroxy-3-pyridinesulfonanilide

At room temperature m-aminophenol (11.5 g, 105 mmol) was dissolved in 200 ml of tetrahydrofuran (THF). To this solution was added a THF solution of 5,6-dichloro-3-pyridinesulfonyl chloride (12.3 g, 50 mmol). The reaction mixture was allowed to stir at room temperature overnight with a drying tube attached. The solvent was evaporated to dryness on a rotary evaporator; and the residue was extracted into ethyl acetate (200 ml). The ethyl acetate layer was washed three times with 5 percent HCl (25 ml each) and once with distilled water (25 ml). The ethyl acetate extract was dried over anhydrous magnesium sulfate and evaporated to dryness giving 13.4 g of the sulfonanilide.

Preparation of: 5,6-Dichloro-3-pyridinesulfonyl chloride

5-Amino-2,3-dichloropyridine (20.0 g, 123 mmol) was dissolved in 600 ml conc. HCl, and the solution cooled to 5° C. Sodium nitrate (8.5 g, 123 mmol) in 75 ml water was added dropwise, below the surface of the reaction, at such a rate that the temperature was maintained below 10° C. The reaction was stirred 15 minutes after the addition was complete. This mixture was then added rapidly to a solution of 600 ml acetic acid saturated with sulfur dioxide and containing also cupric chloride dihydrate (1.5 g), the solution cooled to 5° C. The reaction was stirred at 5° C. for 20 minutes, then room temperature for 30 minutes and finally poured into 12 liters ice/water. The resulting solids were filtered off, washed with water, and air-dried. Yield: 17.27 g, 57 percent, m.p. 48°-51° C.

Preparation of: 5-Amino-2,3-dichloropyridine 2,3-Dichloro-5-nitropyridine (50.0 g, 0.26 mol) was dissolved in 500 ml conc. HCl, and the solution cooled to 5° C. Stannous chloride dihydrate (160 g) was added over 30 minutes. The reaction was stirred for 2 hours at 5° C. and then heated on a stram bath for 90 minutes. The mixture was cooled and extracted with ethyl acetate. The organic fractions were washed with 10 percent sodium hydroxide, then dried over anhydrous magnesium sulfate, and the solvent evaporated in vacuo to give 21.8 g (50 percent) of the amine, m.p. 110°-113° C.

Preparation of: 2,3-Dichloro-5-nitropyridine

3-Chloro-5-nitro-2-pyridine (67.3 g, 0.385 mol) was added to a mixture of 150 ml phosphorus oxychloride and 70 g phosphorus pentachloride and the mixture refluxed for 17 hours. The excess phosphorus oxychloride was distilled off in vacuo and the remaining residue slurried on 800 ml ice/water. The resulting solids were filtered off, crushed, slurried with additional cold water, filtered off, and air-dried. Yield: 67.2 g, 90 percent, m.p. 110°-113° C.

Preparation of: 3-Chloro-5-nitro-2-pyridone

5-Nitro-2-pyridone (Aldrich Chemical Company) (100 g, 0.71 mol) was added to 1 liter conc. HCl at room temperature, followed by the dropwise addition of a solution of potassium chlorate (87.5 g, 0.71 mol) in 1.2 liter water. A solid material formed during the addition. The mixture was stirred overnight, filtered, and the collected material recrystallized from 50 percent aqueous ethanol. The yield was 77.2 g, 62 percent, m.p. 196°-198° C.

EXAMPLE 2

Synthesis sequence for the preparation of a representative negative redox dye-releaser

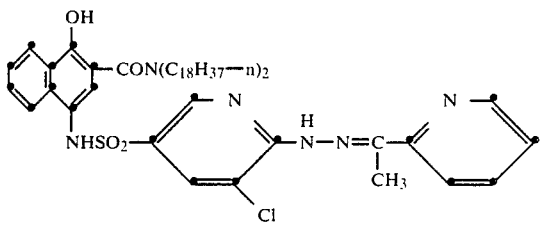

4-Amino-1-hydroxy-N,N-di-n-octadecyl-2-naphthamide (U.S. Pat. No. 4,135,929) and 5,6-dichloro-3-pyridinesulfonyl chloride (above, Example 1) react in pyridine solution to produce the sulfonamide I. In a manner analogous to the sequence in Example 1, the 6-chloro substituent on the pyridine ring is displaced by hydrazine; and the resulting 6-hydrazino compound reacts with 2-acetylpyridine to prepare the sulfonamidonaphthol dye-releaser:

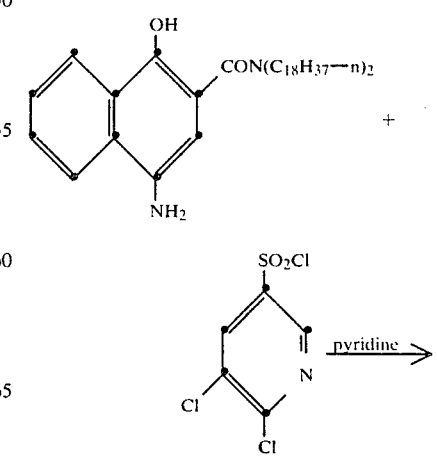

-continued

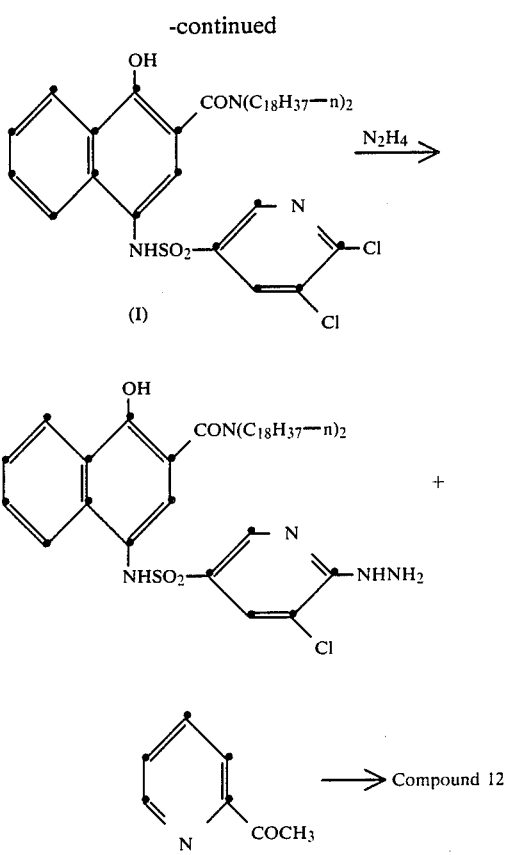

EXAMPLE 3

Released Dyes—Spectra, Light Stability and Dye Diffusion Tests

A receiving element was prepared comprising a poly(ethylene terephthalate) film support having thereon a nickel sulfate hexahydrate (0.64 g/m$^2$)/gelatin (1.08 g/m$^2$) metal complexing layer, and a poly)N-vinylimidazole)/gelatin mordant layer (each at 2.15 g/m$^2$).

An alternative receiving element was used with the premetallized dye-complexes. It comprised a poly(ethylene terephthalate) film support having thereon a layer of gelatin (1.1 g/m$^2$) and a mordant layer of poly(styrene-co-1-vinylimidazole-co-3-benzyl-1-vinylimidazolium chloride (50:40:10) (4.5 g/m$^2$) and gelatin (2.2 g/m$^2$).

The appropriate receiving element was immersed in an alkaline solution of each of the dyes listed in the Table below. The receiver was removed from the dye solution, washed in distilled water, placed in a pH 7.0 buffer solution and dried. Transmission spectra obtained on each sample of the mordanted dyes were normalized by computer to a density of 1.0. The $\lambda_{max}$ at maximum density, along with the "half bandwidth" (HBW), the wavelength range of the curve at half the maximum density, are recorded in the Table below. A narrow HBW generally designates a purer hue.

The above receiving elements at pH 7 were then subjected to 10 days irradiation by a high intensity daylight (HID), 6000 W Xenon arc lamp, the sample receiving 50,000 lux through a Wratten 2B (ultraviolet) filter at approximately 38° C. at low humidity. The percent fade represents the loss in density at $\lambda_{max}$ after irradiation.

The released dyes in the Table were also subjected to a dye diffusion test. The test involved dissolving the dye in a viscous composition and transferring it through a receiving element which contains an opaque and reflecting layer in addition to the mordant layer. The receiver for this test had the following composition (coverages are parenthetically given in g/m$^2$):

A transparent poly(ethylene terephthalate) film support coated with (1) a mordant layer of poly(styrene-co-N-vinylbenzyl-N-benzyl-N, N-dimethylammonium chloride-co-divinylbenzene) (2.28) and gelatin (2.28);

(2) an opaque and reflecting layer of carbon black (1.88) in gelatin (1.23) and titanium dioxide (16.1) in gelatin (2.63); and (3) an overcoat layer of gelatin (4.3).

Dye Diffusion Test

Approximately 0.075 mmol of the unmetallized released dye was dissolved in 10 ml of 0.125N potassium hydroxide. After the dye was completely dissolved, 20 ml of a viscous composition was added; and the resulting solution, stirred for at least 20 minutes, was 0.0025M in dye at a pH of 13.4. The viscous composition was prepared from 46.2 g potassium hydroxide and 54 g carboxymethylcellulose dissolved in 1200 ml water. The dye solution was then spread between the receiver and a clear polyester cover sheet between spaced rollers so that the gap containing the viscous solution had a thickness of 102 μm. Measurement of the rate of dye diffusion was commenced at the point at which half of the laminate had passed through the rollers. The appearance of dye on the mordant was measured at $\lambda_{max}$ as diffuse reflection density vs. time. The reflection density was converted to transmission density by computer with the aid of a mathematical relation derived from a previous calibration. A plot of transmission density, which is proportional to concentration vs. time, was derived; and the value of t-½ of dye transfer, the time in seconds required to obtain one-half of the maximum transmission density, calculated. The following results were obtained:

TABLE

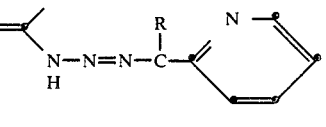

| Cmpd. | A | B | R | λ_max (nm) | HBW (nm) | Dye Fade (%) | Dye Diffusion t₁ (sec) |
|---|---|---|---|---|---|---|---|
| A | $-SO_2NH_2$ | $-OCH_3$ | $CH_3$ | 465 | 70 | 3.3 | 29 |
| B | $-SO_2NH_2$ | $-OCH_3$ | H | 466 | 73 | 13 | — |
| C | $-SO_2NH_2$ | H | H | 455 | 60 | 9 | 25 |
| D | $-SO_2NH_2$ | H | 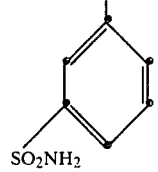 | 455[1] | — | — | — |
| E | $-SO_2NH_2$ | Cl | H | 456 | 60 | — | 29 |
| F | 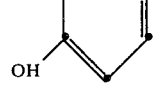 | Cl | H | 460 | 65 | 4 | 41 |
| G | 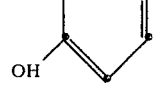 | Cl | $CH_3$ | 456 | 69 | — | 36(25)[2] |
| H | 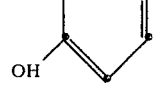 | Cl | H | 459 | 64 | — | 37(28)[2] |
| I[4] | $-SO_2NH_2$ | H | H | 479[3] | — | — | — |
| J[4] | 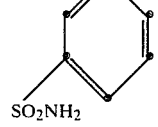 | Cl | H | 464 | 70 | 11 | — |

[1]Solution spectrum in 3:1 dioxane/aqueous pH 7 buffer + excess Ni(2+).
[2]Alkaline solution used to generate the value in parentheses contained additionally 5 g/l ethylenediaminetetraacetic acid, dipotassium salt.
[3]Solution spectrum in dimethylformamide.
[4]Premetallized compound, alternative receiving element.

The above results indicate that the premetallized compounds and released dyes of the compounds according to the invention have a relatively narrow HBW, indicating a purer hue, had relatively low fade and had good diffusibility.

The invention has been described in detail with particular reference to preferred embodiments thereof, but it will be understood that variations and modifications can be effected within the spirit and scope of the invention.

What is claimed is:

1. In a photographic element comprising a support having thereon at least one photosensitive silver halide emulsion layer, said emulsion layer having associated therewith a dye image-providing material, the improvement wherein said dye image-providing material is a nondiffusible compound capable of releasing at least one diffusible yellow dye moiety or precursor thereof having the formula:

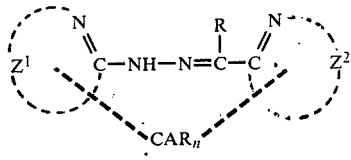

wherein:
(a) $Z^1$ and $Z^2$ each independently represents the atoms necessary to complete a 5- or 6-membered aromatic heterocyclic ring;
(b) CAR represents a ballasted carrier moiety capable of releasing said diffusible yellow dye moiety or precursor thereof as a function of development of said silver halide emulsion layer under alkaline conditions;
(c) R represents hydrogen, an alkyl or substituted alkyl group of from 1 to about 12 carbon atoms, an aryl or substituted aryl group of from about 6 to about 12 carbon atoms, a substituted or unsubstituted 5- or 6-membered aromatic heterocyclic ring, or CAR; and
(d) n is 0, 1 or 2, with the proviso that when n is 0, then R is CAR.

2. The photographic element of claim 1 wherein said dye image-providing material comprises a coordination complex of said nondiffusible compound and a polyvalent metal ion.

3. The photographic element of claim 1 wherein $Z^1$ and $Z^2$ each independently represents the atoms necessary to complete a substituted or unsubstituted pyridine, quinoline, benzothiazole, pyrimidine or quinoxaline ring.

4. The photographic element of claim 1 wherein R represents hydrogen, methyl, ethyl, substituted propyl, butyl, phenyl, substituted phenyl, pyridine, substituted pyridine, pyrimidine or benzothiazole.

5. The photographic element of claim 1 wherein $Z^1$ and $Z^2$ each independently represents the atoms necessary to complete a pyridine or substituted pyridine ring.

6. The photographic element of claim 5 wherein R represents hydrogen, methyl, or pyridine, n is 1 and CAR is attached to the pyridine ring of $Z^1$.

7. The photographic element of claim 1 wherein CAR is a group having the formula:

(Ballast - Carrier - Link) - wherein:
(a) Ballast is an organic ballasting radical of such molecular size and configuration as to render said compound nondiffusible in said photographic element during development in an alkaline processing composition;
(b) Carrier is an oxidizable acyclic, carbocyclic or heterocyclic moiety; and
(c) Link represents a group which, upon oxidation of said carrier moiety, is capable of being hydrolytically cleaved to release said diffusible dye moiety or precursor thereof.

8. The photographic element of claim 7 wherein the carrier moiety contains atoms according to the following configuration:

$$a(-C=C)_b-$$

wherein:
b is a positive integer of 1 to 2; and
a represents the radicals OH, SH, NH—, or hydrolyzable precursors thereof.

9. The photographic element of claim 1 wherein CAR is a group having the formula:

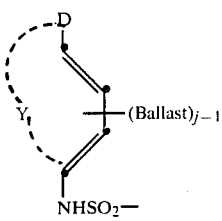

wherein:
(a) Ballast is an organic ballasting radical of such molecular size and configuration as to render said compound nondiffusible in said photographic element during development in an alkaline processing composition;
(b) D is $OR^1$ or $NHR^2$ wherein $R^1$ is hydrogen or a hydrolyzable moiety and $R^2$ is hydrogen or a substituted or unsubstituted alkyl group of 1 to 22 carbon atoms;
(c) Y represents the atoms necessary to complete a benzene nucleus, a naphthalene nucleus, or a 5- to 7-membered heterocyclic ring; and
(d) j is a positive integer of 1 to 2 and is 2 when D is $OR^1$ or when $R^2$ is hydrogen or an alkyl group of less than 8 carbon atoms.

10. The photographic element of claim 9 wherein D is OH, j is 2 and Y is a naphthalene nucleus.

11. The photographic element of claim 1 wherein said nondiffusible compound is:

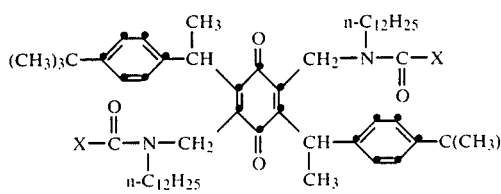

wherein

X is

-continued

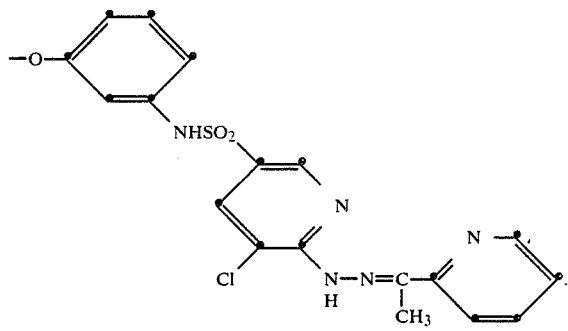

12. In a photographic assemblage comprising:
(i) a support having thereon at least one photosensitive silver hailde emulsion layer having associated therewith a dye image-providing material;
(ii) a dye image-receiving layer; and
(iii) an alkaline processing composition and means containing same for discharge within said assemblage; said assemblage containing a silver halide developing agent; the improvement wherein said dye image-providing material is a nondiffusible compound capable of releasing at least one diffusible yellow dye moiety or precursor thereof having the formula:

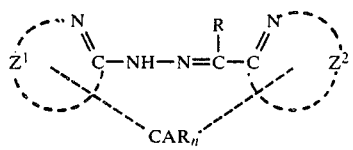

wherein:
(a) $Z^1$ and $Z^2$ each independently represents the atoms necessary to complete a 5- or 6-membered aromatic heterocyclic ring;
(b) CAR represents a ballasted carrier moiety capable of releasing said diffusible yellow dye moiety or precursor thereof as a function of development of said silver halide emulsion layer under alkaline conditions;
(c) R represents hydrogen, an alkyl or substituted alkyl group of from 1 to about 12 carbon atoms, an aryl or substituted aryl group of from about 6 to about 12 carbon atoms, a substituted or unsubstituted 5- or 6-membered aromatic heterocyclic ring, or CAR; and
(d) n is 0, 1 or 2, with the proviso that when n is 0, then R is CAR.

13. The photographic assemblage of claim 12 wherein $Z^1$ and $Z^2$ each independently represents the atoms necessary to complete a substituted or unsubstituted pyridine, quinoline, benzothiazole, pyrimidine or quinoxaline ring.

14. The photographic assemblage of claim 12 wherein R represents hydrogen, methyl, ethyl, substituted propyl, butyl, phenyl, substituted phenyl, pyridine, substituted pyridine, pyrimidine or benzothiazole.

15. The photographic assemblage of claim 12 wherein $Z^1$ and $Z^2$ each independently represents the atoms necessary to complete a pyridine or substituted pyridine ring.

16. The photographic assemblage of claim 15 wherein R represents hydrogen, methyl, or pyridine, n is 1 and CAR is attached to the pyridine ring of $Z^1$.

17. The photographic assemblage of claim 12 wherein said dye image-receiving layer or a layer adjacent thereto contains metal ions.

18. The photographic assemblage of claim 17 wherein:
(a) said dye image-receiving layer is located between said support and said silver halide emulsion layer; and
(b) said assemblage also includes a transparent cover sheet over the layer outermost from said support.

19. The photographic assemblage of claim 18 wherein said cover sheet has thereon, in sequence, a neutralizing layer and a timing layer.

20. The photographic assemblage of claim 19 wherein said discharging means is a rupturable container containing said alkaline processing composition and an opacifying agent, said container being so positioned during processing of said assemblage that a compressive force applied to said container will effect a discharge of the container's contents between said transparent sheet and the layer outermost from said support.

21. The photographic assemblage of claim 17 wherein said support having thereon said photosensitive silver halide emulsion layer is opaque and said dye image-receiving layer is located on a separate transparent support superposed over the layer outermost from said opaque support.

22. The photographic assemblage of claim 21 wherein said transparent support has thereon, in sequence, a neutralizing layer, a timing layer and said dye image-receiving layer.

23. In an integral photographic assemblage comprising:
(a) a photosensitive element comprising a transparent support having thereon the following layers in sequence: a dye image-receiving layer, an alkaline solution-permeable, light-reflective layer, an alkaline solution-permeable, opaque layer, a red-sensitive silver halide emulsion layer having a ballasted cyan dye releaser associated therewith, a green-sensitive silver halide emulsion layer having a ballasted magenta dye releaser associated therewith, and a blue-sensitive silver halide emulsion layer having a ballasted yellow dye releaser associated therewith;
(b) a transparent sheet superposed over said blue-sensitive silver halide emulsion layer and comprising a transparent support having thereon, in sequence, a neutralizing layer and a timing layer; and
(c) a rupturable container containing an alkaline processing composition and an opacifying agent which is so positioned during processing of said assemblage that compressive force applied to said container will effect a discharge of the container's contents between said transparent sheet and said blue-sensitive silver halide emulsion layer; said assemblage containing a silver halide developing agent; the improvement wherein said ballasted yellow dye releaser is a nondiffusible compound capable of releasing at least one diffusible yellow dye moiety or precursor thereof having the formula:

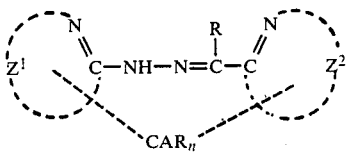

wherein:
(a) $Z^1$ and $Z^2$ each independently represents the atoms necessary to complete a 5- or 6-membered aromatic heterocyclic ring;
(b) CAR represents a ballasted carrier moiety capable of releasing said diffusible yellow dye moiety or precursor thereof as a function of development of said silver halide emulsion layer under alkaline conditions;
(c) R represents hydrogen, an alkyl or substituted alkyl group of from 1 to about 12 carbon atoms, an aryl or substituted aryl group of from about 6 to about 12 carbon atoms, a substituted or unsubstituted 5- or 6-membered aromatic heterocyclic ring, or CAR; and
(d) n is 0, 1 or 2, with the proviso that when n is 0, then R is CAR.

24. The photographic assemblage of claim 23 wherein said dye image-receiving layer or a layer adjacent thereto contains metal ions.

* * * * *